United States Patent [19]
Beach et al.

[11] Patent Number: 5,420,372
[45] Date of Patent: May 30, 1995

[54] ALPHA-OLEFIN OLIGOMERS USEFUL AS BASE STOCKS AND VISCOSITY INDEX IMPROVERS, AND LUBRICATING OILS CONTAINING SAME AND METHOD OF MAKING THE OLIGOMERS

[75] Inventors: David L. Beach; Paul G. Bercik, both of Kingwood, Tex.; Neal E. Morganson, Novato, Calif.

[73] Assignee: Chevron Chemical Company, San Francisco, Calif.

[21] Appl. No.: 998,500

[22] Filed: Dec. 30, 1992

Related U.S. Application Data

[60] Division of Ser. No. 267,056, Nov. 4, 1988, Pat. No. 5,177,276, which is a continuation of Ser. No. 17,496, Feb. 24, 1987, abandoned, which is a continuation-in-part of Ser. No. 5,994, Jan. 21, 1987, abandoned, which is a continuation of Ser. No. 744,998, Jun. 17, 1985, abandoned.

[51] Int. Cl.$^6$ .............................................. C07C 2/08
[52] U.S. Cl. .................................. 585/522; 585/7; 585/10; 585/18; 585/523
[58] Field of Search ............... 585/522, 524, 511, 512, 585/7, 10, 18, 523; 502/103

[56] References Cited
U.S. PATENT DOCUMENTS

| | | | |
|---|---|---|---|
| 3,876,528 | 4/1975 | Heilman et al. | 585/10 |
| 4,085,064 | 4/1978 | Wristers | 502/104 |
| 4,827,064 | 5/1989 | Wu | 585/10 |
| 5,177,276 | 1/1993 | Beach et al. | 585/523 |

*Primary Examiner*—Anthony McFarlane
*Attorney, Agent, or Firm*—W. K. Turner; C. J. Caroli; E. A. Schaal

[57] ABSTRACT

An alpha-olefin oligomer consisting essentially of repeating units having the structural formula:

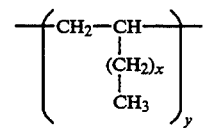

wherein
x represents an integer from 3 to 11, inclusive; and
y represents the number of repeating units in the oligomer such that the weight average molecular weight is from about 5,000 to about 20,000;

said oligomer having from about 70 to 100 percent head-to-tail alignment of the repeating units of the oligomer. Preferably the weight average molecular weight of the oligomer is from 5,000 to about 10,000; and said oligomer is further characterized as having a dispersity of less than about 5.5, and a Z average molecular weight of less than about 24,000.

24 Claims, No Drawings

ALPHA-OLEFIN OLIGOMERS USEFUL AS BASE STOCKS AND VISCOSITY INDEX IMPROVERS, AND LUBRICATING OILS CONTAINING SAME AND METHOD OF MAKING THE OLIGOMERS

CROSS-REFERENCE TO RELATED APPLICATIONS

This application is a division of application Ser. No. 267,056, filed Nov. 4, 1988, now U.S. Pat. No. 5,177,276, which is a continuation of application Ser. No. 017,496, filed Feb. 24, 1987, now abandoned, which is a continuation-in-part of application Ser. No. 005,994, filed Jan. 21, 1987, now abandoned, which is a continuation of application Ser. No. 744,998, filed Jun. 17, 1985, now abandoned.

FIELD OF THE INVENTION

The present invention relates to viscosity index improvers for lubricating oils and to lubricating oil compositions containing such viscosity index improvers. More particularly, the present invention relates to liquid, alpha-olefin oligomeric shear stable viscosity index improvers for lubricating oils and to lubricating oils having an improved viscosity index containing alpha-olefin oligomeric shear stable viscosity improvers. The shear stable alpha-olefin oligomers of the invention are also useful as viscosity enhancing base oils, either neat or in blends where high viscosity industrial lubricants are desired.

BACKGROUND OF THE INVENTION

Petroleum oils have been conventionally used as lubricating oils in internal combustion engines. In the past, a thinner, lighter weight oil had to be used in colder climates in order to provide sufficient fluidity for initial lubrication at low temperatures. However, as the engine continued to operate and heat up the oil, the oil became thinner and at higher operating temperatures had insufficient viscosity for optimum lubrication. In warm weather operation a heavier weight oil was required, because the thinner, lighter weight oil provided insufficient lubrication at such higher temperatures. The viscosity-temperature relationship of an oil is expressed as its "viscosity index".

In order to improve the viscosity index of lubricating oils, it has been proposed to incorporate various polymeric materials into the base stock in order to improve the inherent viscosity-temperature characteristics of the lubricating oil. One common class of commercial polymeric viscosity index improvers are the methacrylate polymers, such as polymethacrylate esters. High molecular weight viscosity modifiers formed from alpha-olefin polymers have been proposed, such as those having a weight average molecular weight in excess of 50,000 as described in U.S. Pat. No. 3,795,616 to Heilman et al.

Lower molecular weight alpha-olefin oligomers and copolymers have been proposed for use as base fluids, such as those produced, and thereafter hydrogenated, using boron trifluoride and a co-catalyst, such as n-butanol described in U.S. Pat. No. 4,032,591 to Cupples et al. However, such hydrogenated oligomers have had little or no effect when attempts have been made to utilize small amounts of such materials as viscosity index improvers for lubricating oils.

The aforementioned U.S. Pat. No. 3,795,616 to Heilman et al describes polymers of alpha-olefins having from 5 to 12 carbon atoms which are useful as viscosity enhancers for lubricating oils. The alpha-olefin polymers of Heilman et al are high molecular weight materials having a weight average molecular weight between 50,000 and 1,000,000 and a ratio of weight average to number average molecular weight of from 1 to 12. Heilman et al also teach that any Ziegler-Natta type catalyst can be employed to prepare these polymers.

U.S. Pat. No. 3,346,498 to DeVries describes high molecular weight copolymers of alpha-olefins and di-olefins having 11 to 15 carbon atoms which lower the pour point of waxy mineral lubricating oils. These polymers are taught as having a molecular weight of 50,000 to 1,000,000 and are prepared using a catalyst containing a titanium halide and an organo aluminum compound.

Canadian Patent No. 734,980 to Sauer et al discloses lower molecular weight polymers of alpha-olefins having 6 to 16 carbon atoms which are useful as synthetic lubricating oils having a high viscosity index. The polymers of Sauer et al are described as having an average molecular weight ranging from about 300 to 2,000. These polymers are prepared using a catalyst of titanium tetrachloride and an organo aluminum compound, wherein the molar ratio of titanium to aluminum is from 2:1 to 20:1. Sauer et al teach that this molar ratio is important to produce normally liquid polymers. If the molar ratio of titanium to aluminum is below 2:1, Sauer et al teach that undesirable solid polymers are produced.

U.S. Pat. No. 3,403,197 to Seelbach et al discloses low molecular weight unsaturated polymers of alpha-olefins having from 3 to 40 carbon atoms. The polymers of Seelbach et al are described as having a cryoscopic molecular weight of from 150 to 1,500 and are prepared using a catalyst consisting of violet titanium trichloride and a monoalkyl aluminum dihalide.

SUMMARY OF THE INVENTION

A liquid alpha-olefin oligomer has been found which provides exceptional viscosity index improvement when admixed with a lubricating oil base stock comprising either a petroleum or synthetic base oil.

Moreover, the alpha-olefin oligomer itself has been found to be very effective as a viscosity enhancing base oil, which also exhibits unexpectedly good shear stability. Accordingly, the present invention provides a normally liquid alpha-olefin oligomer consisting essentially of repeating units having the structural formula:

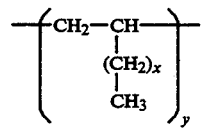

wherein
  x represents an integer from 3 to 11, inclusive; and
  y represents the number of repeating units in the oligomer such that the weight average molecular weight is from about 5,000 to about 20,000;
said oligomer having from about 70 to 100 percent head-to-tail alignment of the repeating units of the oligomer. Preferably the weight average molecular weight of the oligomer is from 5,000 to about 10,000; and said oligomer is further characterized as having a dispersity of less than about 5.5, and a Z average molecular weight of less than about 24,000.

By the expression "70 to 100 percent head-to-tail alignment" is meant that from 70 to 100 percent of each oligomer molecule is a block of monomer units connected head-to-tail or by 1-2 addition. For example, in the oligomerization of 1-decene, if the first (head) carbon atom in every 1-decene monomer molecule joins with another 1-decene monomer molecule by binding to its second (tail) carbon atom, this would be 100 percent head-to-tail alignment.

According to another aspect of the present invention, a lubricating oil composition is provided comprising a lubricating oil base stock, such as a petroleum or synthetic oil, and an alpha-olefin oligomer of the present invention.

According to a further aspect of the present invention, a one-step process is provided for producing the normally liquid alpha-olefin oligomers of the invention, which process comprises contacting, as the sole polymerizable compound, an alpha-olefin having from 6 to 14 carbon atoms with a catalyst comprising the purple form of titanium trichloride and an alkyl aluminum compound selected from the group consisting of trialkyl aluminum, dialkyl aluminum hydride, alkyl aluminum dihydride, dialkyl aluminum halide and alkyl aluminum sesquihalide, in the presence of free molecular hydrogen. The alpha-olefin oligomers produced by the present process will generally have a bromine index of from about zero to about 2,000.

Moreover, when carrying out the process of the invention, a mixture of alpha-olefins having from 6 to 14 carbon atoms per molecule may be employed to produce oligomers having repeating units derived from two or more different alpha-olefin monomers. Accordingly, the present invention also provides a normally liquid alpha-olefin oligomer consisting essentially of repeating units having the structural formula:

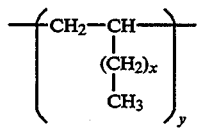

wherein
x represents an integer from 3 to 11, inclusive, and x can be variable from one repeating unit to another;
y represents the number of repeating units in the oligomer such that the weight average molecular weight is from about 5,000 to about 20,000;
said oligomer having from about 70 to 100 percent head-to-tail alignment of the repeating units of the oligomer.

DESCRIPTION OF THE PREFERRED EMBODIMENTS

The alpha-olefin oligomers of the present invention are produced by oligomerizing an alpha-olefin monomer having from 6 to about 14 carbon atoms per molecule, or mixtures thereof. The term "oligomerization" is employed herein to describe the conversion of the $C_6$ to $C_{14}$ alpha-olefin monomers to a higher molecular weight normally liquid product having a weight average molecular weight in the range of from about 5,000 to about 20,000, preferably from about 5,000 to about 10,000.

As indicated, suitable monoolefins include alpha-olefin monomers having from about 6 to about 14 carbon atoms, such as 1-hexene, 1-heptene, 1-octene, 1-nonene, 1-decene, 1-undecene, 1-dodecene, 1-tridecene and 1-tetradecene, preferably from 1-octene to 1-dodecene, and more preferably from 1-octene to 1-decene. An especially preferred alpha-olefin is 1-decene. Mixtures of these alpha-olefins can also, of course, be employed.

The alpha-olefin monomer is contacted with a catalyst containing the purple form of titanium trichloride and an alkyl aluminum compound selected from the group consisting of trialkyl aluminum, dialkyl aluminum hydride, alkyl aluminum dihydride, dialkyl aluminum halide and alkyl aluminum sesquihalide. In general, the alkyl group can have from about 1 to 8 carbon atoms, preferably from about 2 to 4 carbon atoms.

Suitable alkyl aluminum compounds include, for example, trimethyl aluminum, triethyl aluminum, triisobutyl aluminum, tri-normal octyl aluminum, diisobutylaluminum hydride, isobutyl aluminum dihydride, diethylaluminum chloride, diisobutylaluminum chloride and ethylaluminum sesquichloride. Preferred alkyl aluminum compounds are the dialkyl aluminum hydrides, such as diisobutylaluminum hydride, and the alkyl aluminum sesquichlorides, such as ethylaluminum sesquichloride. An especially preferred alkyl aluminum compound is diisobutylaluminum hydride.

The purple form of titanium trichloride can either be used preformed, or generated in situ by reduction of $TiCl_4$. The purple $TiCl_3$ should have a general crystal structure which is hexagonal, or cubic close packed, or a mixture of hexagonal and cubic close packed, with a bulk density of 40 to about 100 pounds per cubic foot, preferably from about 60 to about 90 pounds per cubic foot. Such crystals should have an average particle size distribution of from about 5 microns to about 200 microns, preferably from about 10 to about 100 microns. In general, higher surface areas promote higher activities. Thus, especially preferred surface areas are from about 10 to about 100 square meters per gram, preferably from about 30 to about 70 square meters per gram.

Suitable oligomerization temperatures include, for example, temperatures of from about 0° to about 200° C., preferably from about 25° to about 150° C., with from about 60° to about 120° C. being more preferred.

The oligomerization reaction is conducted in the presence of a suitable molecular weight regulator, such as hydrogen or diethylzinc. Hydrogen is the preferred molecular weight regulator.

Another unexpected benefit for the process of this invention where hydrogen is used, is the production in one step of an alpha-olefin oligomer product having an unexpectedly low bromine index, indicating the oligomer is being saturated during the processing. This oligomer saturation is unexpected due to the use of relatively low total pressures and low hydrogen partial pressures. The prior art, for example, Canadian Patent No. 734,980 to Sauer et al, and U.S. Pat. No. 3,795,616 to Heilman et al, teach the use of hydrogen in the oligomerization step solely as a molecular weight control agent. Sauer et al teach the subsequent hydrogenation of their very low molecular weight oligomers to produce a desired saturated product. It is a distinct benefit to the process of this invention to produce substantially saturated oligomers as a product of the oligomerization step without the need for a second stage or subsequent hydrogenation step.

The oligomerization pressure is suitable from about 1 to about 175 atmospheres, preferably from about 5 to about 25 atmospheres total pressure. If hydrogen is used as the molecular weight regulator, suitable hydrogen partial pressures can be from about 1 to about 158 psig (1 to about 11.75 atmospheres), preferably from about 60 to about 120 psig (4.08 to about 8.13 atmospheres).

As noted above, an added advantage of the process of this invention is that a substantially fully-saturated product can be obtained which does not require post hydrogenation. The obtention of this substantially fully-saturated product is a function of the particular catalyst employed, the catalyst concentration, and other reaction conditions. For example, when the catalyst employed is diisobutyl aluminum hydride, the use of a relatively low partial pressure of hydrogen of 100 psig resulted not only in the use of hydrogen as a molecular weight control agent, but also in the production of a substantially fully-saturated product, that is, one having a bromine index of less than about 500. Higher hydrogen partial pressures within the range noted above may be required with other catalysts to produce a substantially saturated oligomer product in one step.

Additionally, it has been found that there is some saturation of the alpha-olefin feed during the oligomerization process conducted in the presence of hydrogen. The unconverted feed, which usually contains from about 50 to 100, more usually 80 to 100, weight percent saturated alpha-olefin, can be, if desired, recycled to the oligomerization process to serve as the reaction solvent.

The oligomerization reaction can be conducted in either batch, semi-continuous, or continuous reaction.

If desired, a diluent may be employed for the oligomerization reaction. Suitable diluents include hydrocarbon solvents, such as pentane, hexane, heptane, and the like, naphtha, gasoline fractions, kerosene, gas oil fractions, furnace oil fractions, light lubricating oils, heavy lubricating oils, and the like. In one preferred embodiment, the diluent is the saturated form of the alpha-olefin charge stock which, as noted above, can be formed in situ and recycled to the process. Organic hydrocarbon solvents, such as benzene, toluene, the xylenes, and the like, and chlorinated hydrocarbon solvents are less preferred. A solvent is not required, since the oligomeric product is a pourable liquid. However, if desired, the aforesaid diluent can be used in amounts of from about 10 to about 90 weight percent, preferably from about 30 to about 70 weight percent.

The amount of purple titanium trichloride employed in the catalyst is generally from about 0.1 to about 1.5 weight percent of the alpha-olefin feed. The molar ratio of titanium to aluminum in the catalyst will generally range from about 0.2:1 to 4:1, preferably from about 0.3:1 to 1.3:1, and more preferably will be about 1:1.

Suitable oligomerization reaction times include from about 5 minutes to about 20 hours, preferably from about 10 minutes to about 5 hours, with from about 30 minutes to about 3 hours being especially preferred.

In addition to the fact that the oligomers of the invention are saturated during the oligomerization process, thus eliminating the need for an expensive secondary hydrogenation process, the high viscosity oligomers of this invention can be recovered by simple distillation at normal pressures as a total bottoms product. The overhead from the distillation recovers the reaction solvent and, at times, the unconverted feed and the total oligomer product can be directly recovered as a bottoms product. For the higher carbon number olefin feeds, for example, 1-decene, a vacuum distillation is preferred to recover the unconverted feed. The raw oligomer product is preferably washed with dilute hydrochloric acid to remove catalyst residues and then water washed until neutral, prior to recovery by distillation.

Oligomerization catalysts and conditions are selected to provide an oligomeric product having a weight average molecular weight of from about 5,000 to about 20,000, preferably from about 5,000 to about 10,000, and more preferably from about 6,500 to about 8,000. Moreover, the resulting structure of the oligomeric product of the present invention contains from about 70 to about 100 percent head-to-tail alignment of the repeating units in the oligomer, preferably from about 90 to about 100 percent head-to-tail alignment.

The dispersity, or distribution factor, is defined as the ratio of weight average molecular weight to number average molecular weight, that is, $\overline{M}w/\overline{M}n$. For the alpha-olefin oligomers of the present invention, the dispersity should generally be less than 5.5, and preferably will be between about 2.5 and 4.5. In order to achieve the desired dispersity, the number average molecular weight for the oligomers of the invention will generally range from about 1,000 to about 4,000, preferably from about 1,000 to about 2,500.

In addition, the Z average molecular weight for the alpha-olefin oligomers of the present invention will normally be less than about 24,000, and usually from about 14,000 to 20,000.

The weight average molecular weight, number average molecular weight and Z average molecular weight for the alpha-olefin oligomers of the invention are determined by gel permeation chromatography. For decene-1 oligomers, the chromatography column was calibrated with polydecene-1 oligomers of known molecular weight. The methods of calculation and definitions of the above molecular weight terms are discussed, for example, in "The Elements of Polymer Science and Engineering—An Introductory Text for Engineers and Chemists", by Alfred Rudin, Chapter Two, Page 53, Academic Press, 1982.

The molecular weight distribution of the alpha-olefin oligomers of the invention, in terms of area percent using gel permeation chromatography, lies within a relatively narrow range. In general, the molecular weight distribution will be such that less than 40 percent, and preferably less than 29 percent, of the oligomer of the invention will have a molecular weight greater than 9,000. Moreover, less than 10 percent, and preferably less than 5 percent, of the oligomer of the invention will have a molecular weight greater than 29,000.

The alpha-olefin oligomers of the invention possess very high viscosities, which makes these oligomers highly suitable as viscosity enhancing base stocks, either neat or in blends where high viscosity industrial lubricants or greases are desired. In general, the oligomers of the invention, having the preferred weight average molecular weight of about 5,000 to about 10,000, will have viscosities in the range of about 150 to 1250 centistokes (cs.), preferably in the range of about 150 to 500 cs., and more preferably, about 250 to 400 cs., at 210° F., as determined by ASTM D445.

The alpha-olefin oligomers of the invention have also been found to exhibit excellent shear stability. In general, the oligomers of the invention will have a shear stability of less than 10 percent, preferably less than 6 percent, and more preferably less than 4 percent, as measured by the average percentage loss in kinematic viscosity at 100° F. and 210° F. of 3 weight percent blends of the alpha-olefin oligomer of the invention in lubricating oil base stocks of $C_{20}$ to $C_{50}$ carbon number after 30 minutes of sonic shearing at 100° F.

Another important property of the alpha-olefin oligomers of the invention is their low bromine index, which generally ranges from about zero to about 2,000, and preferably will be less than about 750.

The alpha-olefin oligomers of the present invention have additionally been found to possess excellent viscosity index improving characteristics.

Surprisingly, the oligomeric product of the present invention provides exceptional viscosity index improvement to both petroleum base oils and synthetic base oils, while using only minor amounts of the viscosity index improving oligomers of the present invention.

Thus, from about 0.5 to about 40, preferably from about one to about 15, weight percent of the viscosity index improving oligomer of the present invention provide excellent improvement in the viscosity index of petroleum base stocks, such as conventional mineral oil base stocks or base stock blends with or without conventional additives. Additionally, such amounts of the viscosity index improving oligomers of the present invention may be added to synthetic lubricating oils, such as those produced from polymerized alpha-olefins, Fisher-Tropsch produced oil, or the like. In general, the base stocks employed with the present oligomer will have a viscosity at 210° F. of from about 2 to about 100 cs. The amount of base stock present in these lubricating oil compositions will generally range from about 60 to 99.5 weight percent of the total composition. Mixtures of petroleum base oils and synthetic base oils may also be employed.

The viscosity index improving oligomers of the present invention provide not only significant improvement in viscosity index to such base stocks, but, in addition, have improved shear stability as compared with those resulting from the use of higher molecular weight viscosity index improvers.

Accordingly, the preferred lubricating oil compositions comprise a lubricating oil base stock and a minor viscosity index improving amount, that is, about 1.0 to 15 weight percent, of the oligomer of the invention, and said oligomer having a viscosity of about 150 to about 500 cs. at 210° F. will generally exhibit a shear stability of less than about 10%, as measured by the average percentage loss in kinematic viscosity at 100° F. and 210° F. after 30 minutes of sonic shearing at 100° F.

The lubricating oil compositions provided by the viscosity index improving oligomers of the present invention provide a product having a viscosity of from about 2.5 to about 150 cs. at 210° F., as determined by ASTM D445.

The following examples are presented to illustrate the invention. All percentages are by weight except where otherwise indicated. The viscosity measurements that are used herein are the kinematic viscosities in centistokes (cs.) as determined by ASTM D445. The viscosity indexes were determined by ASTM D2270 and the various oligomer analyses were determined by gel permeation chromatography.

EXAMPLES

Examples 1-8

The monomer, 1-octene, was introduced into a one-liter autoclave (Hastalloy B) which had been previously purged with dry nitrogen. In addition, 12 milliliters of a heptane solution containing 24.5 weight percent $Al(C_2H_5)_3$ and 300 milliliters of dry, oxygen-free n-heptane along with sufficient purple titanium trichloride (obtained from the Stauffer Chemical Company under the designation 2.1AA) is added to provide a weight ratio of 4.5 millimoles of triethyl aluminum per millimole of $TiCl_3$. The autoclave was pressured to 280 psig (18.79 atmospheres) with hydrogen and the contents of the autoclave were vigorously stirred while heating to maintain a temperature of 100° C.

After continuing the reaction for 2.5 hours, excess hydrogen was vented and the autoclave contents were drained into 500 milliliters of water. The reactor was then flushed with 700 milliliters of n-heptane, which was then combined with the drained product. Next, 25 milliliters of a 10% hydrogen chloride solution was added to the drained product and the resulting solution stirred vigorously for 2 hours. The resulting organic layer was separated and dried over sodium sulfate. Subsequent filtration yielded a clear, water-white solution, and heptane was removed by means of rotary evaporation.

The weight average molecular weight of the resulting material is estimated to be about 12,000 and contained about 90 percent of a head-to-tail alignment of the repeating units of the molecules forming the oligomer.

The resulting oligomer was blended into a light neutral petroleum oil having a 210° F. viscosity of 4.11 cs., a 100° F. viscosity of 21.62 cs., a viscocity index of 99, and a pour point of $-5°$ F., in amounts sufficient to provide 3.0 weight percent of the oligomer in the neutral oil. The foregoing procedure was repeated with varying ratios of purple titanium trichloride to triethyl aluminum. The results are shown in Table I below.

TABLE I

| EXAMPLE NO. | 1 | 2 | 3 | 4 | 5 | 6 | 7 | 8 |
|---|---|---|---|---|---|---|---|---|
| Oligomer Yield % of Charge | | 79 | 84 | 60 | 96 | 97 | 98 | 98 |
| Ratio of triethyl aluminum/$TiCl_3$ mmole/mmole | | 4.5 | 3.4 | 2.7 | 1.4 | 0.89 | 0.45 | 0.27 |
| Oligomer Concentration Wt. % | 0 | 3 | 3 | 3 | 3 | 3 | 3 | 3 |
| Viscosity, cs. | | | | | | | | |
| 0° F. ($-17.8°$ C.) | — | — | 2593 | 2146 | 2488 | 2770 | 3005 | 3489 |
| 100° F. (37.8° C.) | 21.62 | 33.09 | 35.67 | 33.11 | 40.35 | 43.31 | 50.62 | 52.67 |
| 210° F. (98.9° C.) | 4.11 | 6.06 | 6.60 | 6.13 | 7.35 | 7.94 | 9.15 | 9.54 |
| Viscosity Index | 99 | 144 | 154 | 148 | 161 | 169 | 177 | 180 |
| Pour Point (°F.) | $-5$ | 0 | 0 | $+10$ | $+0$ | $+5$ | $+5$ | $+10$ |

As seen from Table I, under the heading Example 1, it can be seen that the base oil has a viscosity index of 99. However, with the addition of only 3 weight percent oligomeric viscosity index improver, the viscosity index of the resultant blend was increased to a range of from 144 to 180, which corresponds to an improvement of from 31 to 82 percent in the viscosity index of the blend. Likewise, the addition of the viscosity index improver significantly increased the viscosity of the base oil at each temperature. Thus, for example, the viscosity at 210° F. for the base oil was 4.11, but was increased to from about 6 to 9.54 with the addition of the viscosity index improver. Accordingly, Examples 1-8 demonstrate the significant improvement provided by only small amounts of the viscosity index improver of the present invention when utilized with a petroleum oil base stock.

Examples 9-20

A mixture including 1.9 grams of purple TiCl₃ (commercially available from Stauffer Chemical Company as Stauffer 2.1AA), 12 milliliters of a heptane solution containing 24.5% by weight of aluminum triethyl, 250 grams of 1-decene and 250 grams of dry, oxygen-free n-heptane were added to a one-liter stainless steel autoclave that had been previously purged with dry nitrogen. The autoclave was pressured to 200 psig (16.67 atmospheres) with hydrogen, and the contents were vigorously stirred with cooling to maintain the temperature at less than 30° C.

The reaction is exothermic, and when the exotherm had ceased, 100 milliliters of water were added with rapid stirring to decompose the catalyst. Additional n-heptane was then added, the reaction product heated to 60° C., and the solution removed from the autoclave. The resulting material was diluted to a total volume of 3500 milliliters with n-heptane and the organic layer was separated from the aqueous phase. Fifty grams of sodium sulfate were added to the organic solution and the resulting mixture stirred at 80°-90° C. and then filtered to provide a clear, water-white solution. Heptane was removed by means of rotary evaporation and a steam bath.

In order to test the oligomer as a viscosity index improver for synthetic base oils, the liquid oligomer was dissolved in a polyalpha-olefin synthetic fluid that had a viscosity of 8 cs. to provide a 50% by weight concentrate.

Separate portions of the concentrate containing the oligomeric viscosity index improver were blended with a polyalpha-olefin (PAO) synthetic fluid having a viscosity of 4 cs. (commercially available from Chevron Corporation under the trademark "SYNFLUID"). The results are set forth in Table II, below.

TABLE II

| | Experimental Blend 1 | | | |
|---|---|---|---|---|
| Example No. | 9 | 10 | 11 | 12 |
| 1-Decene Oligomer, Wt. % | 0 | 2 | 5 | 10 |
| PAO Synthetic Base Stock | 100 | 98 | 95 | 90 |
| Viscosity, cs., 40° C. | 18.43[1/] | 26.68 | 47.61 | 102.6 |
| 100° C. | 3.98[2/] | 5.99 | 10.31 | 21.26 |
| Viscosity Index | 125 | 181 | 213 | 245 |
| Pour Point, °F. | −65 | −65 | −65 | −65 |

[1/]100° F. (37.8° C.)
[2/]210° F. (98.9° C.)

As seen in Table II, the addition of 2, 5 and 10 weight percent of the oligomeric viscosity index improver significantly increased the viscosity index of the synthetic base stock from 125 to from 181 to 245 with no change in the pour point of the resultant lube oil.

For comparative purposes, the foregoing procedure was repeated using a polyalpha-olefin synthetic fluid having a viscosity of 6 cs. The results are shown in Table III below.

TABLE III

| | Experimental Blend 2 | | | |
|---|---|---|---|---|
| Example No. | 13 | 14 | 15 | 16 |
| 1-Decene Oligomer, Wt. % | 0 | 2 | 5 | 10 |
| PAO Synthetic Base Stock | 100 | 98 | 95 | 90 |
| Viscosity, cs., | | | | |
| 40° C. | 33.82[1/] | 50.56 | 81.85 | 175 |
| 100° C. | 5.99[2/] | 9.51 | 15.01 | 31.02 |
| Viscosity Index | 135 | 175 | 194 | 222 |
| Pour Point, °F. | −65 | −65 | −65 | −65 |

[1/]100° F. (37.8° C.)
[2/]210° F. (98.9° C.)

Once again, it is seen that the addition of the viscosity index improver significantly increases the viscosity index of the synthetic base fluid while also building the viscosity of the synthetic base stock.

As a further comparison, the foregoing procedure was repeated with a synthetic fluid having a viscosity of 8 cs., and the test results are shown in Table IV, below.

TABLE IV

| | Experimental Blend 3 | | | |
|---|---|---|---|---|
| Example No. | 17 | 18 | 19 | 20 |
| 1-Decene Oligomer, Wt. % | 0 | 2 | 5 | 10 |
| PAO Synthetic Base Stock | 100 | 98 | 95 | 90 |
| Viscosity, cs., 40° C. | 46.46 | 69.55 | 114.5 | 226 |
| 100° C. | 7.73 | 11.63 | 18.77 | 35.59 |
| Viscosity Index | 134 | 163 | 184 | 220 |
| Pour Point, °F. | −65 | −65 | −65 | −65 |

Once again, it is seen that the addition of relatively small amounts of the viscosity index improver of the present invention not only builds the viscosity of the base fluid, but increases the viscosity index to from 134 up to from 163 to 220 depending upon the amount of viscosity index improver. Moreover, it is seen that the addition of only 2 weight percent of the viscosity index improver increases the viscosity index of the base fluid to from 134 to a range of from 163-220.

Examples 21-24

The synthesis procedure of Examples 9-20 was repeated using 222 grams of 1-decene at a reaction temperature of 100° C. for 3.5 hours. The reaction system involved the use of 300 milliliters of n-heptane with a weight ratio of aluminum triethyl to titanium trichloride of 2 to 1.

The hydrogen pressure was 100 psig (6.71 atmospheres). The resulting oligomer was blended with the light neutral mineral oil of Example 1 in a 3% by weight amount.

For comparative purposes, the foregoing procedure was repeated for two additional runs, with the exception that the hydrogen pressure was varied, so that in one run the hydrogen pressure was 150 psig (10 atmospheres), while in the third run, the hydrogen pressure was 400 psig (26.8 atmospheres).

Each of the resulting oligomer fractions was admixed with a sample of the identical light neutral mineral oil of Example 1 using 3% by weight of the oligomer. The resultant blends were tested and the results are set forth below in Table V.

TABLE V

Oligomer Additives + Light Neutral Mineral Oil Blends

| Example No. | 21 | 22 | 23 | 24 |
|---|---|---|---|---|
| Oligomer, Wt. % of blend | 0 | 3 | 3 | 3 |
| Hydrogen Pressure, psig (atm.) | | 100(6.7) | 150(10) | 400(26.8) |
| Viscosity, cs. | | | | |
| 210° F. (98.9° C.) | 4.11 | 6.66 | 9.44 | 5.41 |
| 100° F. (37.8° C.) | 21.62 | 36.73 | 52.39 | 29.04 |
| Viscosity Index | 99 | 150 | 178 | 135 |
| Pour Point, °F. | −5 | −5 | −5 | −5 |

As seen in Table V, in a comparison of Examples 21 and 22, the use of the addition of 3% by weight of the oligomer of the present invention improves the viscosity index of the base oil from a value of 99 to 150 which constitutes a 51% increase with no detrimental effect on the pour point. As seen in a comparison of Example 21 with Example 23, the oligomer provided using a hydrogen pressure of 150 resulted in an increase in the viscosity index of the base fluid from 99 to 178 which is an 80% increase using only 3 weight percent of the viscosity index improving oligomer of the present invention.

As seen from a comparison of Example 21 with the results in Example 24, where the hydrogen pressure was more than double that of Example 23, the viscosity index of the blend was 135 which constituted a 36% increase in the viscosity index of the base fluid. However, such improvement is below that achieved using a much lower hydrogen pressure for producing the oligomer.

Example 25

The synthesis procedure of Examples 21-24 was repeated using 300 ml n-heptane, 220 g 1-decene, 0.5 g purple TiCl3, and 6 ml of a 25 percent by weight solution of triethylaluminum in n-heptane at a reaction temperature of 100° C. and a hydrogen pressure of 380 psig (25.5 atmospheres) for 3.5 hours. The oligomer product had a viscosity of 336 cs. at 210° F. and a sonic shear overall average viscosity loss of 5.2% after 30 minutes of sonic shearing at 100° F., based on 100° F. and 210° F. viscosities of 3 weight percent blends in a light neutral distillate and 4 cs. SYNFLUID ® PAO, a synthetic polyalpha-olefin oil.

Example 26

The synthesis procedure of Example 25 was repeated, except that the hydrogen pressure used was 340 psig (22.8 atmospheres). The oligomer product had a viscosity of 406 cs. at 0° C. and a sonic shear overall average viscosity loss of 4.9% after 30 minutes of sonic shearing at 100° F., based on 100° F. and 210° F. viscosities of 3 weight percent blends in a light neutral distillate and 4 cs. SYNFLUID ® PAO, a synthetic polyalpha-olefin oil.

Examples 27-37

Examples 27-37 show the oligomerization of 1-decene using a purple TiCl3/diisobutyl aluminum hydride catalyst in a molar ratio of 0.94-1.04 moles of diisobutyl aluminum hydride per mole of purple TiCl3. The amount of purple TiCl3 (Stauffer, Grade AA, Type 2.1) employed was equal to 1.0-1.5 weight percent of the 1-decene feed. The oligomerization reactions of Examples 27-37 were carried out according to the following general procedure:

With the exception of Example 35, these reactions were made in a 50-gallon glass-lined Pfaudler stirred tank reactor which had previously been purged with dry nitrogen. The dry, oxygen-free n-heptane solvent was initially added in an amount equal to the decene-1 feed subsequently added. The desired amount of alkyl solution (25 weight percent in n-heptane solvent) was then pressured into the reactor directly from an alkyl cylinder. The TiCl3 was added into the reactor via a closed addition apparatus that was previously loaded in a controlled nitrogen atmosphere dry box. The slurry of catalyst in solvent was then heated to within a few degrees of the desired reaction temperature in less than an hour's time. At such temperature, dry and oxyen-free hydrogen was injected to pressure the reactor to the desired reaction pressure. Then the dry, oxygen-free decene was metered into the reactor at a constant rate over at least about a forty-minute period, during which time the reaction pressure and temperature were maintained at the desired levels. During the decene feed addition periods of 40 to 55 minutes, for Examples 27-37, temperatures averaged 100° to 115° C. and pressures averaged 77 to 98 psig. The reaction was continued for 90 to 161 minutes after the decene was added. During the post feed addition reaction period, temperatures averaged 100° to 110° C. and pressures averaged 95 to 100 psig. At this point the oligomerization reactions were essentially complete and hydrogen uptake had stopped. The reactants were quickly cooled to about 60° C., depressured, and transferred to a wash tank where the catalyst was removed by repeated washings with dilute aqueous hydrogen chloride solutions. Any residual hydrogen chloride is removed by repeated water washings. The washed product was batch-distilled to a pot temperature of about 175° C. at about 3 mm Hg to remove all the solvent and essentially all the decene not oligomerized. Example 35 was a small scale reaction conducted in a 4-liter stainless steel stirred autoclave. The general procedure used in this small scale reaction was the same as that described below for Examples 38-44. The operating conditions used, however, were in the range noted directly above.

The results of these oligomerizations are set forth in Table VI. As seen in Table VI, the 1-decene oligomers of the present invention exhibit excellent viscosity and shear stability characteristics, as well as a very low bromine index. In addition, the 1-decene oligomers of the invention have very low levels of residual chlorine.

TABLE VI

Oligomerization of 1-Decene Using a Purple TiCl3/Diisobutyl Aluminum Hydride Catalyst

| Example No. | 27 | 28 | 29 | 30 | 31 | 32 | 33 | 34 | 35[a] | 36 | 37 |
|---|---|---|---|---|---|---|---|---|---|---|---|
| Yield, wt. % Decene | 71.0 | 66.3 | 63.3 | 75.1 | 73.5 | 73.3 | 75.5 | 74.7 | 70.3 | 74.9 | 73.8 |
| Viscosity, cs. @ 210° F. | 137.6 | 163 | 215 | 331.9 | 345 | 369 | 393.7 | 420 | 444 | 457 | 459 |

TABLE VI-continued

Oligomerization of 1-Decene Using a Purple TiCl₃/Diisobutyl Aluminum Hydride Catalyst

| Example No. | 27 | 28 | 29 | 30 | 31 | 32 | 33 | 34 | 35[a] | 36 | 37 |
|---|---|---|---|---|---|---|---|---|---|---|---|
| Sonic Shear, 30 min at 100° F. Overall Average[b] | | | | | | | | | | | |
| Viscosity Loss: % | 1.4 | 1.9 | 2.8 | 2.5 | 3.6 | 3.6 | 3.5 | 3.7 | 2.6 | 3.9 | 4.2 |
| Viscosity Index Loss: % | 1.2 | 1.3 | 2.6 | 0.8 | 3.8 | 3.1 | 1.1 | — | 2.2 | 2.5 | 3.7 |
| Gel Permeation Chromatography | | | | | | | | | | | |
| $M_n$ | 1439 | 1683 | 1772 | 1926 | 2046 | 1909 | 1942 | 2080 | 1838 | 2121 | 2155 |
| $M_w$ | 5282 | 5746 | 6267 | 6993 | 7340 | 7426 | 7277 | 7458 | 7999 | 7621 | 7725 |
| $M_z$ | 16643 | 13526 | 14142 | 16243 | 19209 | 19498 | 17456 | 15876 | 18335 | 15998 | 16239 |
| Dispersity, $M_w/M_n$ | 3.67 | 3.41 | 3.54 | 3.63 | 3.59 | 3.89 | 3.75 | 3.59 | 4.35 | 3.59 | 3.58 |
| Distribution, Area % | | | | | | | | | | | |
| 28896+ | 1.3 | 1.2 | 1.5 | 2.2 | 2.4 | 2.4 | 2.3 | 2.4 | 3.5 | 2.5 | 2.6 |
| 22323+ | 2.5 | 2.9 | 3.7 | 4.7 | 5.3 | 5.4 | 5.1 | 5.4 | 7.3 | 5.7 | 5.9 |
| 8918+ | 16.0 | 19.5 | 22.4 | 25.6 | 27.0 | 27.4 | 27.1 | 28.4 | 30.2 | 29.4 | 29.8 |
| 1218-8918 | 59.1 | 59.1 | 57.9 | 57.2 | 56.7 | 55.5 | 56.3 | 56.0 | 51.8 | 55.5 | 55.3 |
| 569-1218 | 13.6 | 12.5 | 11.2 | 9.8 | 9.6 | 9.4 | 9.3 | 9.0 | 9.4 | 8.7 | 8.6 |
| <569 | 11.3 | 8.9 | 8.5 | 7.4 | 6.7 | 7.7 | 7.3 | 6.6 | 8.6 | 6.4 | 7.3 |
| Bromine Index | 232 | 280 | 413 | 306 | 331 | 339 | 329 | 329 | 216 | 484 | 481 |
| Chlorine, wt. % | <0.01 | <0.01 | <0.01 | <0.01 | <0.01 | <0.01 | <0.01 | <0.01 | <0.01 | <0.01 | <0.01 |

[a]4 l Zipperclave reactor
[b]Based on 100° F. and 210° F. viscosities of 3 wt. % blends in a Light Neutral Distillate and 4 centistoke SYNFLUID ® PAO, a synthetic polyalpha-olefin oil.

Examples 38-44

Examples 38-44 show the oligomerization of 1-decene using a purple TiCl₃/ethyl aluminum sesquichloride catalyst in a molar ratio of 0.97-1.06 moles of ethyl aluminum sesquichloride per mole of purple TiCl₃. The amount of purple TiCl₃ (Stauffer, Grade AA, Type 2.1) employed was equal to 0.5-1.5 weight percent of the 1-decene feed. The oligomerization reactions of Examples 38-44 were carried out according to the following general procedure:

With the exception of Examples 39 and 44, these reactions were made in a four-liter stainless steel stirred autoclave which had previously been purged with dry nitrogen. The TiCl₃ was added to the dry reactor via a closed glass ampoule. The reactor was then closed and purged exhaustively with nitrogen before a portion of the dry, oxygen-free n-heptane solvent was added. The desired amount of alkyl solution (25 wt. % in n-heptane solvent) was added to the reactor via a syringe which was inserted through a ball valve on the solvent-decene feed inlet port, while maintaining a nitrogen blanket on the reactor. Another portion of the solvent was then pumped in. Afterward, the ampoule containing the TiCl₃ was broken by turning on the reactor agitator at maximum speed. Then a remaining portion of the solvent was pumped into the reactor. The total amount of solvent was the same as the amount of decene added subsequently. The slurry of catalyst in solvent was then heated to within a few degrees of the desired reaction temperature in less than an hour's time. At such temperature, dry and oxygen-free hydrogen was injected to pressure the reactor to the desired reaction pressure. Then the dry and oxygen-free decene was metered into the reactor at a constant rate over at least about a forty-minute period during which time the reaction pressure and temperature were maintained at the desired levels. During the decene feed addition periods of 37 to 68 minutes for Examples 38-44, temperatures averaged 95° to 100° C. and pressures averaged 88 to 100 psig. The reaction was continued 87 to 90 minutes after the decene was added. During the post feed addition reaction period, temperatures averaged 100° to 105° C. and pressures averaged 94 to 108 spig. At this point, the oligomerization reactions were essentially complete and hydrogen uptake had stopped. The reactants were quickly cooled to about 60° C., depressured, and transferred to a wash tank where the catalyst was removed by repeated washing with dilute aqueous hydrogen chloride solutions. Any residual hydrogen chloride is then removed by repeated water washings. The washed product was batch-distilled to a pot temperature of about 175° C. at about 3 mm Hg to remove all the solvent and essentially all the decene not oligomerized. Examples 39 and 44 were large scale reactions conducted in 50-gallon Pfaudler glass-lined stirred tank reactor. The general procedure used in these two large scale reactions was the same as that described previously for Examples 27-37. The operating conditions used, however, were in the range noted directly above.

These results of these oligomerization reactions are set forth in Table VII. As seen in Table VII, the 1-decene oligomers of the present invention possess excellent viscosity and shear stability characteristics. Moreover, the 1-decene oligomers of the invention have a low bromine index and a low level of residual chlorine.

It has also been found that 3 weight percent of the 1-decene oligomers shown in Tables VI and VII very effectively enhanced the viscosity of the light neutral distillate and the 4 cs. SYNFLUID ® synthetic oil in the blends used to measure sonic shear stability. These 1-decene oligomers of the invention blended to a significantly greater viscosity than that predicted, based on the conventional method of calculating the viscosity of a mixture.

Moreover, 3 weight percent of the 1-decene oligomers shown in Tables VI and VII also very effectively improved the viscosity index of the light neutral distillate and the 4 cs. SYNFLUID® synthetic oil in the blends used to measure sonic shear stability. stability of less than 10 percent, as measured by the average percentage loss in kinematic viscosity at 100° F.

TABLE VII

| | Oligomerization of 1-Decene Using a Purple TiCl₃/Ethyl Aluminum Sesquichloide Catalyst | | | | | | |
|---|---|---|---|---|---|---|---|
| Example No. | 38 | 39(a) | 40 | 41 | 42 | 43 | 44(a) |
| Yield, wt. % Decene | 79.8 | 76.9 | 69.5 | 77.6 | 70.3 | 57.5 | 58.0 |
| Viscosity, cs. @ 210° F. | 199 | 337 | 381 | 398 | 482.3 | 707 | 825.5 |
| Sonic Shear, 30 min @ 100° F. Overall Average(b) | | | | | | | |
| Viscosity Loss, % | 2.31 | 2.34 | 2.73 | 3.87 | 5.20 | 3.86 | 5.53 |
| Viscosity Index Loss % | 1.97 | 2.36 | 2.62 | 3.37 | 5.49 | 3.23 | 4.75 |
| Gel Permeation Chromatography | | | | | | | |
| Mn | 1250 | 1724 | 1574 | 1615 | 1547 | 1978 | 2053 |
| Mw | 5988 | 7488 | 7890 | 7193 | 7800 | 8967 | 9547 |
| Mz | 16273 | 17785 | 19573 | 16159 | 19543 | 19938 | 21094 |
| Dispersity, Mw/Mn | 4.79 | 4.34 | 5.00 | 4.45 | 5.04 | 4.53 | 4.65 |
| Distribution, Area % | | | | | | | |
| 28896+ | 2.2 | 3.3 | 3.7 | 2.5 | 3.5 | 4.8 | 5.7 |
| 22323+ | 4.7 | 6.8 | 7.4 | 5.8 | 7.1 | 9.4 | 10.7 |
| 8918+ | 21.5 | 27.3 | 28.9 | 27.5 | 29.6 | 34.1 | 36.2 |
| 1218–8918 | 47.0 | 52.6 | 49.4 | 51.7 | 49.0 | 49.4 | 47.8 |
| 569–1218 | 16.5 | 10.5 | 10.2 | 10.2 | 9.7 | 8.3 | 8.1 |
| <569 | 15.0 | 9.6 | 11.5 | 10.6 | 11.7 | 8.2 | 7.9 |
| Bromine Index | 1723 | 364 | 1239 | 1151 | 1138 | 697 | 410 |
| Chlorine, Wt. % | 0.12 | 0.04 | 0.11 | 0.10 | 0.11 | 0.05 | 0.03 |

(a)50-Gallon Pfaudler reactor
(b)Based on 100° F. and 210° F. viscosities of 3 wt. % blends in a Light Neutral Distillate and 4 centistoke SYNFLUID ® PAO, a synthetic polyalpha-olefin oil.

What is claimed is:

1. A one-step process for producing a normally liquid alpha-olefin oligomer having a bromine index of from about zero to about 2,000 and consisting essentially of repeating units having the structural formula:

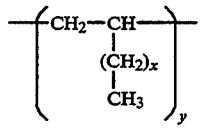

wherein x represents an integer from 3 to 11, inclusive; and y represents the number of repeating units in the oligomer such that the weight average molecular weight is from about 5,000 to about 20,000; said oligomer having from about 70 to 100 percent head-to-tail alignment of the repeating units of the oligomer; which process comprises contacting, as the sole polymerizable compound, an alpha-olefin having from 6 to 14 carbon atoms with a catalyst comprising the purple form of titanium trichloride and an alkyl aluminum compound selected from the group consisting of trialkyl aluminum, dialkyl aluminum hydride, alkyl aluminum dihydride, dialky aluminum halide and alkyl aluminum sesquihalide, in the presence of free molecular hydrogen, and wherein the process is conducted at a temperature of from about 0° C. to about 200° C. and a total pressure of from about one to about 175 atmospheres.

2. The process according to claim 1, wherein the weight average molecular weight of the oligomer is from about 5,000 to about 10,000.

3. The process according to claim 2, wherein said oligomer is further characterized as having a dispersity of less than about 5.5, and a Z average molecular weight of less than about 24,000.

4. The process according to claim 3, wherein x is an integer from 5 to 7, inclusive, and said alpha-olefin oligomer has a dispersity of from about 2.5 to 4.5 and is further characterized as having a viscosity of from about 150 to 1250 centistokes at 210° F. and a shear and 210° F. of 3 weight percent blends of the alpha-olefin oligomer in lubricating oil base stocks of $C_{20}$ to $C_{50}$ carbon number after 30 minutes of sonic shearing at 100° F.

5. The process according to claim 1, wherein the process is conducted at a temperature of from about 60° C. to about 120° C. and a total pressure of from about 5 to about 25 atmospheres.

6. The process according to claim 1, wherein the alpha-olefin is 1-decene.

7. The process according to claim 1, wherein the molar ratio of titanium to aluminum in the catalyst is from about 0.2:1 to 4:1.

8. The process according to claim 7, wherein the molar ratio of titanium to aluminum in the catalyst is from about 0.3:1 to 1.3:1.

9. The process according to claim 1, wherein the amount of purple titanium trichloride is about 0.1 to 1.5 weight percent of the alpha-olefin employed.

10. The process according to claim 1, wherein the purple titanium trichloride has a crystal structure which is hexagonal or cubic close packed, or a mixture thereof, and a surface area of from about 10 to about 100 square meters per gram.

11. The process according to claim 10, wherein the purple titanium trichloride has a surface area of from about 30 to about 70 square meters per gram.

12. The process according to claim 10, wherein the purple titanium trichloride has a particle size distribution of from about 5 to about 200 microns.

13. The process according to claim 12, wherein the purple titanium trichloride has a particle size distribution of from about 10 to about 100 microns.

14. The process according to claim 1, wherein the alkyl aluminum compound is selected from the group consisting of trimethyl aluminum, triethyl aluminum, triisobutyl aluminum, tri-normal octyl aluminum, diisobutylaluminum hydride, isobutyl aluminum dihydride, diethylaluminum chloride, diisobutylaluminum chloride and ethylaluminum sesquichloride.

15. The process according to claim 14, wherein the alkyl aluminum compound is selected from the group consisting of diisobutylaluminum hydride, isobutyl aluminum dihydride, diethylaluminum chloride, diisobutylaluminum chloride and ethylaluminum sesquichloride.

16. The process according to claim 1, wherein the alkyl aluminum compound is a dialkyl aluminum hydride or an alkyl aluminum sesquichloride.

17. The process according to claim 14, wherein the alkyl aluminum compound is trimethyl aluminum.

18. The process according to claim 14, wherein the alkyl aluminum compound is triethyl aluminum.

19. The process according to claim 14, wherein the alkyl aluminum compound is triisobutyl aluminum.

20. The process according to claim 15, wherein the alkyl aluminum compound is diisobutylaluminum hydride.

21. The process according to claim 15, wherein the alkyl aluminum compound is diethylaluminum chloride.

22. The process according to claim 15, wherein the alkyl aluminum compound is diisobutylaluminum chloride.

23. The process according to claim 15, wherein the alkyl aluminum compound is ethylaluminum sesquichloride.

24. A one-step process for producing a normally liquid alpha-olefin oligomer having a bromine index of from about zero to about 2,000 and consisting essentially of repeating units having the structural formula:

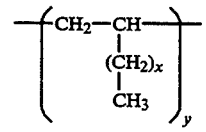

wherein x represents an integer from 3 to 11, inclusive, and x can be variable from one repeating unit to another; and y represents the number of repeating units in the oligomer such that the weight average molecular weight is from about 5,000 to about 20,000; said oligomer having from about 70 to 100 percent head-to-tail alignment of the repeating units of the oligomer; which process comprises contacting an alpha-olefin or mixture of alpha-olefins having from 6 to 14 carbon atoms with a catalyst comprising the purple form of titanium trichloride and an alkyl aluminum compound selected from the group consisting of trialkyl aluminum, dialkyl aluminum hydride, alkyl aluminum dihydride, dialkyl aluminum halide and alkyl aluminum sesquihalide, in the presence of free molecular hydrogen, and wherein the process is conducted at a temperature of from about 0° C. to about 200° C. and a total pressure of from about one to about 175 atmospheres.

* * * * *